(12) United States Patent
Nagai et al.

(10) Patent No.: US 10,899,804 B2
(45) Date of Patent: Jan. 26, 2021

(54) FLUORESCENT PROTEIN

(71) Applicant: Osaka University, Osaka (JP)

(72) Inventors: Takeharu Nagai, Osaka (JP); Hajime Shinoda, Osaka (JP); Tomoki Matsuda, Osaka (JP); Yuanqing Ma, Sydney (AU)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 16/083,144

(22) PCT Filed: Mar. 10, 2017

(86) PCT No.: PCT/JP2017/009759
§ 371 (c)(1),
(2) Date: Sep. 7, 2018

(87) PCT Pub. No.: WO2017/155101
PCT Pub. Date: Sep. 14, 2017

(65) Prior Publication Data
US 2019/0085039 A1    Mar. 21, 2019

(30) Foreign Application Priority Data

Mar. 10, 2016 (JP) ................................ 2016-046953

(51) Int. Cl.
| | |
|---|---|
| *C07K 14/435* | (2006.01) |
| *C07K 19/00* | (2006.01) |
| *C12N 5/10* | (2006.01) |
| *C12N 15/09* | (2006.01) |
| *G01N 21/64* | (2006.01) |
| *G01N 21/78* | (2006.01) |

(52) U.S. Cl.
CPC .. *C07K 14/43504* (2013.01); *C07K 14/43595* (2013.01); *C07K 19/00* (2013.01); *C12N 5/10* (2013.01); *C12N 15/09* (2013.01); *G01N 21/64* (2013.01); *G01N 21/78* (2013.01); *C07K 2319/60* (2013.01)

(58) Field of Classification Search
None
See application file for complete search history.

(56) References Cited

U.S. PATENT DOCUMENTS

2006/0275822 A1  12/2006  Miyawaki et al.
2010/0167394 A1  7/2010  Nagai et al.

FOREIGN PATENT DOCUMENTS

| JP | 2004-187544 A | 7/2004 |
|---|---|---|
| WO | 2009/020197 A1 | 2/2009 |
| WO | 2011/096501 A1 | 8/2011 |

OTHER PUBLICATIONS

Takemoto, K., et al. 2013 Scientific Reports 3(2629): 7 pages. (Year: 2013).*
International Search Report issued in corresponding International Patent Application No. PCT/JP2017/009759 dated Jun. 6, 2017.
Shinoda et al., "An acid insensitive green fluorescent protein from Olindias formosa," BMB2015 (Dai 38 Kai Annual Meeting of the Molecular Biology Society of Japan, Dai, 88 Kai Annual Meeting of the Japanese Biochemical Society Godo Taikai, Koen Yoshishu (2015).
Shinoda et al., "Novel green fluorescent protein from Olindias formosa with exceptional pH stability," Biophysics, 55: Supplement 1-2 (2Pos212) 55: S298, 2015.
Matsuda et al., "Tanryotai-gata Hikari Zokan Keiko Tanpakushitsu SuperNova," The Molecular Biology Society of Japan Dai 37 Kai Annual Meeting of the Molecular Biology Society of Japan, Koen Yoshishu (2014).
Baird et al., "Circular permutation and receptor insertion within green fluorescent proteins," PNAS, 96: 11241-11246 (1999).
Tomosugi et al., "An ultramarine fluorescent protein with increased photostability and pH insensitivity," Nature Methods, 6: 351-353 (2009).
Shinoda et al., "Acid-Tolerant Monomeric GFP from Olindias formosa," Cell Chemical Biology, 25: 1-9 (2018).
"An acid insensitive green fluorescent protein from Olindias formosa," Biochemistry and Molecular Biology (2015).
Saito et al., "Luminescent proteins for high-speed single-cell and whole-body imaging," Nature Communications (2012).
Takai et al., "Expanded palette of Nano-lanterns for real-time multicolor luminescence imaging," PNAS, 112: 4352-4356 (2015).
Suzuki et al., "Five colour variants of bright luminescent protein for real-time multicolour bioimaging," Nature Communications (2016).
Extended European Search Report issued in corresponding European Patent Application No. 17763433.4 dated Oct. 16, 2019.

* cited by examiner

*Primary Examiner* — Marsha Tsay
(74) *Attorney, Agent, or Firm* — Morgan, Lewis & Bockius LLP (57) ABSTRACT

Provided is a green-yellow fluorescent protein with high pH stability (with reduced pH sensitivity). In one or more embodiments, the fluorescent protein is a fluorescent protein comprising an amino acid sequence from position 2 to 225 of the amino acid sequence of SEQ ID NO: 1, at least a mutation being introduced into the sequence, wherein the above-mentioned mutation is selected from the group consisting of F149T or S or A, L158T or S or A, H160T or S or A, Y174T or S or A, and Y192T or S or A as well as combinations of 2 to 5 thereof.

13 Claims, 6 Drawing Sheets

Specification includes a Sequence Listing.

Localization in Intracellular Structure/Protein

Visualization of Acidic Organelle

Scale bar: 20 μm

FLUORESCENT PROTEIN

A computer readable text file, entitled "SequenceListing.txt" created on or about Jun. 23, 2020 with a file size of about 6 kb contains the sequence listing for this application and is hereby incorporated by reference in its entirety.

TECHNICAL FIELD

The present disclosure relates to a green-yellow fluorescent protein with high pH stability, a photo-switching mutant thereof, and a fusion protein thereof, as well as a molecular sensor, DNA, expression cassette, vector, and transformant thereof.

BACKGROUND ART

Fluorescent proteins are widely used as markers capable of tracking the behavior of molecules in vivo in real time or as fluorescence resonance energy transfer (FRET) biosensor production tools for detecting ion concentrations or physiologically active substances (for example, Patent Document 1).

PRIOR ART DOCUMENTS

Patent Documents

[Patent Document 1] JP2004-187544A

SUMMARY OF THE INVENTION

Problem to be Solved by the Invention

However, since most fluorescent proteins have greatly reduced fluorescence intensity in acidic environments, it is difficult to apply them in acidic environments such as lysosomes, secretory granules, and autophagosomes. Currently, cyan and red fluorescent proteins with high pH stability have been reported, but pH stable green-yellow fluorescent proteins have not been reported.

Thus, in one aspect, the present disclosure provides a green-yellow fluorescent protein with high pH stability (with reduced pH sensitivity).

Means for Solving Problem

In one or more embodiments, the present disclosure relates to a fluorescent protein having an amino acid sequence from position 2 to 225 of the amino acid sequence of SEQ ID NO: 1, at least a mutation being introduced into the sequence (hereinafter, also referred to as a monomeric fluorescent protein according to the present disclosure), wherein the above-mentioned mutation is selected from the group consisting of F149T or S or A, L158T or S or A, H160T or S or A, Y174T or S or A, and Y192T or S or A as well as combinations of 2 to 5 thereof.

In one or more other embodiments, the present disclosure relates to a fluorescent protein having an amino acid sequence from position 2 to 232 of the amino acid sequence of SEQ ID NO: 1 or a fluorescent protein that has an amino acid sequence from position 2 to 232 of the amino acid sequence of SEQ ID NO: 1, one to several amino acids of the sequence being deleted, substituted and/or added and that has a pH sensitivity (pKa) of 4.0 or less, is dimeric, and has a green-yellow fluorescent color (hereinafter, a dimeric fluorescent protein according to the present disclosure).

In one or more other embodiments, the present disclosure relates to a photo-switching mutant-type fluorescent protein including a "mutation that results in a photo-switching type" introduced further into a monomeric fluorescent protein according to the present disclosure or a dimeric fluorescent protein according to the present disclosure.

In one or more other embodiments, the present disclosure relates to a fusion protein or a molecular sensor that includes a fluorescent protein according to the present disclosure.

In one or more other embodiments, the present disclosure relates to a nucleic acid including a base sequence that encodes a fluorescent protein, a fusion protein, or a molecular sensor according to the present disclosure, as well as an expression cassette including said base sequence, and a vector or a transformant including them.

Effects of the Invention

In one aspect, the present disclosure can provide a green-yellow fluorescent protein with high pH stability (with reduced pH sensitivity). In one or more non-limiting embodiments, said fluorescent protein allows imaging to be performed in acidic environments and makes it possible to perform cell imaging in acidic cellular environments, such as lysosomes, secretory granules, or autophagosomes.

Furthermore, in one or more non-limiting embodiments, when being combined with a cyan or red fluorescent protein with high pH stability, said fluorescent protein allows, for example, plural types of fluorescence observations to be performed in acidic environments and also makes it possible to obtain biosensors (for example, a FRET biosensor, a biosensor using the circular permutation technique, and a molecular sensor using the split GFP technology) for detecting, for example, ion concentrations or physiologically active substances in acidic environments.

Furthermore, in one or more embodiments, the present disclosure can provide a green-yellow fluorescent protein with high pH stability as a monomer type. Thus, in one or more non-limiting embodiments, when a fusion protein thereof is formed with another protein, the effect of dimerization can be eliminated, which enables effective imaging and detection.

Moreover, in one or more embodiments, a mutant including a "mutation that results in a photo-switching type" introduced further into a monomeric fluorescent protein according to the present disclosure or a dimeric fluorescent protein according to the present disclosure enables super-resolution imaging in environments where the pH fluctuates or in acidic environments.

DESCRIPTION OF EMBODIMENTS

The present disclosure is based on the finding that green-yellow fluorescent proteins derived from flower hat jellies (scientific name: *Olindias formosa*) show good pH stability (i.e., reduced pH sensitivity).

The present disclosure is also based on the finding that a wild-type green-yellow fluorescent protein (hereinafter also referred to as dfGFP; SEQ ID NO: 1) cloned from a flower hat jelly is a dimer and this dfGFP was modified to obtain a monomeric green-yellow fluorescent protein (hereinafter also referred to as mfGFP; SEQ ID NO: 2).

In the present disclosure, the term "green-yellow fluorescent protein" refers to a fluorescent protein having a green or yellow-green fluorescent color, and refers, in one or more embodiments, to one in which the wavelength at which the fluorescence intensity of the emission spectrum is maximized is included in a range of 495 to 570 nm.

In the present disclosure, the term "monomeric green-yellow fluorescent protein" may include all mutants of the monomeric green-yellow fluorescent proteins derived from the amino acid sequence (SEQ ID NO: 1) of green-yellow fluorescent proteins (dfGFP, dimeric) of flower hat jellies.

In the present disclosure, a fluorescent protein being monomeric means that fluorescent proteins of the same species do not polymerize but have the property of existing as a simple substance. Furthermore, in the present disclosure, a fluorescent protein being dimeric means that the fluorescent protein has the property that two fluorescent proteins of the same species interact with each other to form a stable complex.

In the present disclosure, the term "fluorescent protein having an amino acid sequence A" refers to, in one or more embodiments, the fact that the fluorescent protein can include another amino acid such as N-terminal methionine, a signal peptide sequence, an amino acid sequence that allows the protein to be purified, and a combination thereof, at the N-terminus or C-terminus of the amino acid sequence A. The amino acid sequence that allows the protein to be purified can be selected by those skilled in the art.

In the present disclosure, the mutation represented by "$X_1NX_2$" indicates, by a general method of describing a mutation, a mutation in which the amino acid residue $X_1$ (an amino acid residue in one letter code) at position N of the amino acid sequence is substituted with the amino acid residue $X_2$ (an amino acid residue in one letter code).

In the present disclosure, the mutation represented by "$X_1NX_2$ or $X_3$ or $X_4$" indicates a mutation in which the amino acid residue $X_1$ (an amino acid residue in one letter code) at position N of the amino acid sequence is substituted with the amino acid residue $X_2$, $X_3$, or $X_4$ (each indicating an amino acid residue in one letter code).

In the present disclosure, the mutation represented by "$X_1N/X_2(N+1)/X_3(N+2) \rightarrow Y_1Y_2Y_3Y_4$" indicates a mutation in which the three amino acid residues $X_1$, $X_2$, and $X_3$ at positions N to (N+2) of the amino acid sequence are substituted with the four amino acid residues $Y_1$, $Y_2$, $Y_3$, and $Y_4$. Furthermore, the mutation represented by "$X_1N/X_2(N+1)/X_3(N+2) \rightarrow Y_1Y_2Y_3$" indicates a mutation in which the three amino acid residues $X_1$, $X_2$, and $X_3$ at positions N to (N+2) of the amino acid sequence are substituted with the three amino acid residues $Y_1$, $Y_2$, and $Y_3$.

In the present disclosure, the mutation represented by "$X_1NX_2$ or $X_3$ or $X_4$" and the mutation represented by "$X_1N/X_2(N+1)/X_3(N+2) \rightarrow Y_1Y_2Y_3Y_4$" each may be counted as one mutation.

In the present disclosure, $X_1$ and N represented by, for example, "$X_1NX_2$" refer to the amino acid residue $X_1$ at position N of the amino acid sequence of SEQ ID NO: 1 in the Sequence Listing or the amino acid residue $X_1$ at position corresponding to position N of the amino acid sequence of SEQ ID NO: 1 in the Sequence Listing, unless otherwise noted.

In the present disclosure, the pH sensitivity of a fluorescent protein refers to a decrease in fluorescence intensity of the fluorescent protein that occurs when the pH of a medium in which the fluorescent protein is present changes from a basic pH to an acidic pH. In the present disclosure, the pH stability of a fluorescent protein refers to less decrease in fluorescence intensity of the fluorescent protein that occurs when the pH of a medium in which the fluorescent protein is present changes from a basic pH to an acidic pH. The "fluorescence intensity" of a fluorescent protein can be measured using a spectrofluorophotometer.

In the present disclosure, the pH sensitivity (pKa) indicates a pH at which when the pH of a medium in which a fluorescent protein is present changes from a basic pH to an acidic pH, the fluorescence intensity of said fluorescent protein is half the maximum value. Specifically, it can be measured by the method described in the examples.

[Monomeric Green-Yellow Fluorescent Protein]

In one aspect, the present disclosure relates to a monomeric green-yellow fluorescent protein having an amino acid sequence from position 2 to 225 of the amino acid sequence of SEQ ID NO: 1, in which a mutation that results in a monomeric type has been introduced into the sequence.

In one or more embodiments, the "mutation that results in a monomeric type" is a mutation selected from the group consisting of F149T or S or A, L158T or S or A, H160T or S or A, Y174T or S or A, and Y192T or S or A as well as combinations of 2 to 5 thereof. Here, "F149T or S or A" means "F149T, F149S, or F149A", "L158T or S or A" means "L158T, L158S, or L158A", "H160T or S or A" means "H160T, H160S, or H160A", "Y174T or S or A" means "Y174T, Y174S, or Y174A", and "Y192T or S or A" means "Y192T, Y192S, or Y192A".

Accordingly, in one or more embodiments, the present disclosure relates to a fluorescent protein having an amino acid sequence from position 2 to 225 of the amino acid sequence of SEQ ID NO: 1, in which at least a mutation has been introduced into the sequence, wherein the above-mentioned mutation is selected from the group consisting of F149T or S or A, L158T or S or A, H160T or S or A, Y174T or S or A, and Y192T or S or A as well as combinations of 2 to 5 thereof.

The "mutation that results in a monomeric type" or the "mutation introduced into an amino acid sequence from position 2 to 225 of the amino acid sequence of SEQ ID NO: 1" can be any one of F149T or S or A, L158T or S or A, H160T or S or A, Y174T or S or A, or Y192T or S or A, or a combination of 2, 3, 4, or 5 mutations selected from F149T or S or A, L158T or S or A, H160T or S or A, Y174T or S or A, and Y192T or S or A.

Among the above-mentioned "combinations of mutations", examples of a combination of two mutations include, in a non-limiting embodiment, a combination of Y174T or S or A and Y192T or S or A. In another embodiment, examples thereof include a combination of two mutations Y174T and Y192A.

Among the above-mentioned "combinations of mutations", examples of a combination of three mutations include, in a non-limiting embodiment, a combination of F149 T or S or A, L158T or S or A, and H160T or S or A. In another embodiment, examples thereof include a combination of three mutations F149T, L158T, and H160T.

Among the above-mentioned "combinations of mutations", examples of a combination of five mutations include, in a non-limiting embodiment, a combination of F149T or S or A, L158T or S or A, H160T or S or A, Y174T or S or A, and Y192T or S or A. In another embodiment, examples thereof include a combination of five mutations F149T, L158T, H160T, Y174T, and Y192A.

In one or more non-limiting embodiments, with the dimeric dfGFP (SEQ ID NO: 1) becoming monomeric, when a fusion protein thereof is formed with another protein, the effect of dimerization can be eliminated, which enables effective imaging and detection.

In one or more embodiments, in terms of improvement in brightness and/or improvement in solubility, the monomeric green-yellow fluorescent protein according to the present disclosure may further include a mutation selected from the group consisting of K112E or D or Q, E147K or R or Q, Q145E or D, K166E or D or Q, P162L or V or I or A, P223L or V or I or A, N37S or A or G, E140K or R or Q, K185R or A or G, A150/E151/G152→PHGP or PHA, and K180T or S as well as combinations of 2 to 11 thereof that may be introduced thereinto in addition to the aforementioned "mutation that results in a monomeric type." The positions of these mutations are based on SEQ ID NO: 1. In terms of improvement in brightness and/or improvement in solubility, the number of the above-mentioned mutations that can be introduced is 1, 2, 3, 4, 5, 6, 7, 8, 9, 10, or 11 or all in one or more embodiments.

In one or more embodiments, in terms of improvement in brightness and/or improvement in solubility, the monomeric green-yellow fluorescent protein according to the present disclosure may further include a mutation selected from the group consisting of K112E, E147K, Q145E, K166E, P162L, P223L, N37S, E140K, K185R, A150/E151/G152→PHGP, and K180T as well as combinations of 2 to 11 thereof that may be introduced thereinto in addition to the aforementioned "mutation that results in a monomeric type."

In one or more embodiments, in terms of the stability of protein folding, the monomeric green-yellow fluorescent protein according to the present disclosure may include amino acid sequences of the N-terminus and C-terminus of another fluorescent protein (for example, EGFP) added to the N-terminus and C-terminus, respectively, of the sequence from position 2 to 225 of the amino acid sequence of SEQ ID NO: 1. The length of the amino acid sequences to be added is a length of, for example, 6 to 8 amino acids or 7 amino acids.

One or more non-limiting embodiments of the monomeric green-yellow fluorescent protein according to the present disclosure include:

a fluorescent protein having an amino acid sequence from position 8 to 232 of the amino acid sequence of SEQ ID NO: 2, a fluorescent protein having an amino acid sequence from position 2 to 232 of the amino acid sequence of SEQ ID NO: 2, a fluorescent protein having an amino acid sequence from position 8 to 239 of the amino acid sequence of SEQ ID NO: 2, a fluorescent protein having an amino acid sequence from position 2 to 239 of the amino acid sequence of SEQ ID NO: 2, and a fluorescent protein having the amino acid sequence of SEQ ID NO: 2.

The pH sensitivity (pKa) of the monomeric green-yellow fluorescent protein according to the present disclosure is 4.0 or less, preferably less than 4.0, and more preferably 3.9 or less.

In one or more embodiments, the monomeric green-yellow fluorescent protein according to the present disclosure may include mutations other than the above-mentioned mutations as long as the function of a monomeric green-yellow fluorescent protein having a pH sensitivity (pKa) of 4.0 or less can be maintained. Examples of said mutations include deletion, substitution, and/or addition of one to several amino acids, where the expression "one to several" includes 1 to 4, 1 to 3, 1 to 2, or 1 in one or more embodiments.

In one or more embodiments, the monomeric green-yellow fluorescent protein according to the present disclosure is one that has an amino acid sequence, which is at least 90%, 91%, 92%, 93%, 94%, 95%, 96%, 97%, 98%, 99%, or 99.5% of identity with the sequence from position 8 to 232 of the amino acid sequence of SEQ ID NO: 2, and has a pH sensitivity (pKa) of 4.0 or less.

In one or more embodiments, the monomeric green-yellow fluorescent protein according to the present disclosure may be a protein synthesized by chemical synthesis or a recombinant protein produced by gene recombination technology. In one or more embodiments, examples of the method of producing a recombinant protein by gene recombination technology include a method of producing it using a host transformed with an expression vector containing a gene that encodes the monomeric green-yellow fluorescent protein according to the present disclosure or a method of producing it in a cell-free system.

[Photo-Switching Mutant]

In one or more embodiments, the monomeric green-yellow fluorescent protein according to the present disclosure may further include a "mutation that results in an photo-switching type" introduced thereinto. Examples of the "mutation that results in a photo-switching type" include T197A or G, i.e., "T197A or T197G." The position of this mutation is based on the amino acid sequence of SEQ ID NO: 1. Based on the amino acid sequence of SEQ ID NO: 2, the "mutation that results in a photo-switching type" is T204A or G.

Thus, one or more non-limiting embodiments of the photo-switching mutant-type monomeric green-yellow fluorescent protein according to the present disclosure include:

a fluorescent protein having an amino acid sequence from position 8 to 232 of the amino acid sequence of SEQ ID NO: 2, a fluorescent protein having an amino acid sequence from position 2 to 232 of the amino acid sequence of SEQ ID NO: 2, a fluorescent protein having an amino acid sequence from position 8 to 239 of the amino acid sequence of SEQ ID NO: 2, a fluorescent protein having an amino acid sequence from position 2 to 239 of the amino acid sequence of SEQ ID NO: 2, and a fluorescent protein having the amino acid sequence of SEQ ID NO: 2, wherein they have a mutation of T204A or G in the amino acid sequence of SEQ ID NO: 2.

In one or more embodiments, the photo-switching mutant-type monomeric green-yellow fluorescent protein according to the present disclosure is a monomeric green-yellow fluorescent protein that has an amino acid sequence, which is at least 90%, 91%, 92%, 93%, 94%, 95%, 96%, 97%, 98%, 99%, or 99.5% of identity with the sequence from position 8 to 232 of the amino acid sequence of SEQ ID NO: 2 having a mutation of T204A or G, has a pH sensitivity (pKa) of 4.0 or less, and is of an photo-switching type.

In the present disclosure, the photo-switching type fluorescent protein refers to a fluorescent protein capable of reversibly photo-switching the fluorescence (Reversibly Photo-Switchable Fluorescent Protein, RSFP). In the present disclosure, in one or more embodiments, the phrase "photo-switching type reversibly photo-switchable fluorescent protein" refers to a fluorescent protein in which fluorescence on and off can be controlled by irradiations with two lights having different wavelengths and on/off switching can be repeatedly performed.

The photo-switching mutant-type monomeric green-yellow fluorescent protein according to the present disclosure having the above-mentioned "mutation that results in a photo-switching type" is a negative photo-switching type RSFP that changes from non-fluorescent to fluorescent when irradiated with a light having a specific wavelength, which does not cause fluorescence excitation, and changes from fluorescent to non-fluorescent when irradiated with a light used for fluorescence excitation.

In the present disclosure, in the case where simply the phrase "monomeric green-yellow fluorescent protein according to the present disclosure" is used, it may include a monomeric green-yellow fluorescent protein of a photo-switching mutant type.

[Fusion Protein]

In another aspect, the present disclosure provides a fusion protein in which a monomeric green-yellow fluorescent protein according to the present disclosure has been fused with another protein or peptide, wherein the portion of said fluorescent protein can function as a monomeric green-yellow fluorescent protein having a pH sensitivity (pKa) of 4.0 or less.

In the fusion protein according to the present disclosure, in one or more non-limiting embodiments, examples of the protein to be bound (fused) to the monomeric green-yellow fluorescent protein according to the present disclosure include a signal sequence, an expression tag, and a protein (a linker sequence as required). In one or more embodiments, from the viewpoint of imaging, examples of the signal sequence and the protein include signal sequences and proteins that can be localized in cell membranes as well as intracellular cytoskeletons (microfilaments, intermediate filaments, microtubules) and organelles (for example, nuclei, endoplasmic reticula, Golgi bodies, mitochondria, endosomes, and lysosomes) in cells.

Since the monomeric green-yellow fluorescent protein and the fusion protein according to the present disclosure are monomeric and have reduced pH sensitivity, in one or more embodiments, they can be used as fluorescent functional indicators in acidic cellular environments such as lysosomes, secretory granules, and autophagosomes or as fluorescent markers, or they can be used for cell imaging (for example, in vivo imaging).

[Molecular Sensor]

Since the monomeric green-yellow fluorescent protein and the fusion protein according to the present disclosure are green-yellow fluorescent proteins with high pH stability, in one or more non-limiting embodiments, when it is combined with a cyan or red fluorescent protein with high pH stability, for example, it enables a plural types of fluorescence observations in acidic environments and makes it possible to provide a biosensor for detecting, for example, ion concentrations or physiologically active substances in acidic environments.

Therefore, in another aspect, the present disclosure relates to a molecular sensor that has a part or all of the amino acid sequence of the monomeric green-yellow fluorescent protein or the fusion protein according to the present disclosure and that utilizes the fluorescent properties of said protein.

The molecular sensor according to the present disclosure may include all of the molecular sensors that utilize the fluorescent properties of the monomeric green-yellow fluorescent protein according to the present disclosure or the fusion protein according to the present disclosure.

Examples of the molecular sensor according to the present disclosure include, as one or more non-limiting embodiments, a FRET biosensor, a biosensor using a circular permutation technique, and a molecular sensor using the split GFP technology.

Examples of the fluorescence resonance energy transfer (FRET) biosensor include a FRET biosensor in which at least one fluorescent protein component that is used for FRET is a monomeric green-yellow fluorescent protein according to the present disclosure. The molecular sensor according to the present disclosure may be in a form composed of proteins or peptides or may be in a form in which a monomeric green-yellow fluorescent protein or a fusion protein according to the present disclosure is bound to a substance other than a protein.

Examples of the biosensor using the circular permutation technique include a biosensor including a circularly-permuted mutant of a monomeric green-yellow fluorescent protein according to the present disclosure. In the present disclosure, circular permutation refers to a mutation in which new N-terminus and C-terminus are produced in a monomeric green-yellow fluorescent protein according to the present disclosure (that is, said protein is internally split into two) and the original C-terminus and N-terminus are linked by a suitable linker sequence. Circular permutation in fluorescent proteins has been conventionally performed and, for example, Baird et al. (Proc. Natl. Acad. Sci. USA, vol 96, pp 11241-11246, 1999) can be referred to. In one or more embodiments, examples of the biosensor using the circular permutation technique in the present disclosure include a structure in which a peptide or protein binds to the N-terminus and the C-terminus of the circularly-permuted mutant of a monomeric green-yellow fluorescent protein according to the present disclosure. The peptide or protein can be suitably selected according to the object to be sensed.

Examples of the molecular sensor using the split GFP technology include a biosensor utilizing a monomeric green-yellow fluorescent protein according to the present disclosure split into two. With respect to the splitting method, the conventional split GFP technology can be referred to. In one or more embodiments, examples of the biosensor using the split GFP technology in the present disclosure include a structure in which a peptide or protein is bound to each portion of the monomeric green-yellow fluorescent protein according to the present disclosure split into two. The peptide or protein can be suitably selected according to the object to be sensed.

[Nucleic Acid]

In one aspect, the present disclosure relates to a nucleic acid that encodes a monomeric green-yellow fluorescent protein according to the present disclosure, a fusion protein according to the present disclosure, or a molecular sensor according to the present disclosure. In the present disclosure, examples of the nucleic acid include single- or double-stranded DNA selected from synthetic DNA, cDNA, genomic DNA, and plasmid DNA, and transcription products of these DNAs.

An example of the base sequence of the DNA that encodes a monomeric green-yellow fluorescent protein according to the present disclosure is the base sequence represented by SEQ ID NO: 3.

[Expression Cassette]

In one aspect, the present disclosure relates to an expression cassette including a nucleic acid that encodes a monomeric green-yellow fluorescent protein, a fusion protein, or a molecular sensor according to the present disclosure. In said expression cassette, the nucleic acid includes an expression control sequence corresponding to the host cell to be introduced that is operatively linked thereto. Examples of the expression control sequence include a promoter, an enhancer, and a transcription terminator, and in addition, an initiation codon, an intron splicing signal, and a stop codon.

[Vector]

In one aspect, the present disclosure relates to a vector capable of expressing a monomeric green-yellow fluorescent protein according to the present disclosure, a fusion protein, or a molecular sensor. In another aspect, the present disclosure relates to a vector capable of expressing a monomeric green-yellow fluorescent protein according to the present disclosure, a fusion protein according to the present disclosure, or a molecular sensor according to the present disclosure. In one or more embodiments, the vector according to the present disclosure is an expression vector having a nucleic acid or an expression cassette according to the present disclosure.

For the vector according to the present disclosure, an expression vector system according to the cell (host) to be expressed can be suitably selected and used. One or more non-limiting embodiments include plasmid, cosmid, YACs, a virus (for example, adenovirus, retrovirus, or episomal EBV) vector, and a phage vector.

[Transformant]

In one aspect, the present disclosure relates to a transformant that expresses a monomeric green-yellow fluorescent protein, a fusion protein, or a molecular sensor according to the present disclosure. In one or more embodiments, the transformant of the present disclosure is a cell that expresses a monomeric green-yellow fluorescent protein, a fusion protein, or a molecular sensor according to the present disclosure, or a tissue, an organ, or a living body including said cell. Furthermore, in one or more embodiments, the present disclosure relates to a transformant having a nucleic acid or a vector according to the present disclosure. In one or more embodiments, the transformant of the present disclosure can be produced by introducing a nucleic acid, an expression cassette, or a vector of the present disclosure into a host. Examples of the host include animal cells, animal cells excluding human living bodies, plant cells, insect cells, and microorganisms.

[Imaging Method]

In one aspect, the present disclosure relates to an imaging method using a monomeric green-yellow fluorescent protein, a fusion protein, or a molecular sensor according to the present disclosure. In one or more embodiments, the imaging method of the present disclosure includes introducing a monomeric green-yellow fluorescent protein, a fusion protein, or a molecular sensor according to the present disclosure into, for example, cells, and detecting fluorescence signals of the monomeric green-yellow fluorescent protein, the fusion protein, or the molecular sensor according to the present disclosure. In one or more embodiments of the present aspect, the imaging method with respect to human living bodies is not included.

[Imaging Method Using Photo Switching Mutant]

In one aspect, the present disclosure relates to an imaging method using a photo-switching mutant-type monomeric green-yellow fluorescent protein according to the present disclosure, a fusion protein thereof, or a molecular sensor using them. In one or more embodiments of the present aspect, the imaging method with respect to human living bodies is not included. In one or more embodiments, the imaging method of the present disclosure includes introducing a photo-switching mutant-type monomeric green-yellow fluorescent protein of the present disclosure into, for example, cells, performing photo-switching of the photo-switching mutant-type fluorescent protein to switch the fluorescence on or off, and/or detecting the fluorescence signal of the photo-switching mutant-type fluorescent protein. In one or more embodiments, the imaging method of the present disclosure is super-resolution imaging or super-resolution live imaging, and in one or more embodiments, examples thereof include PALM (photoactivated localization microscopy), STORM (stochastic optical reconstruction microscopy), RESOLFT (reversible saturable optical fluorescence transition), NL-SIM (Nonlinear structured illumination microscopy), and SOFI (stochastic optical fluctuation imaging).

[Dimeric Green-Yellow Fluorescent Protein]

In another aspect, the present disclosure relates to a wild-type dimeric green-yellow fluorescent protein (dfGFP, an amino acid sequence from position 2 to 232 of SEQ ID NO: 1) cloned from flower hat jelly (scientific name: *Olindias formosa*) and a mutant of a dimeric green-yellow fluorescent protein that is derived from the amino acid sequence (SEQ ID NO: 1) of the dfGFP and that has a pH sensitivity (pKa) of 4.0 or less.

In one or more embodiments, the dimeric green-yellow fluorescent protein according to the present disclosure may include mutations other than the above-mentioned mutations as long as the function of the dimeric green-yellow fluorescent protein having a pH sensitivity (pKa) of 4.0 or less can be maintained. Examples of said mutations include deletion, substitution, and/or addition of one to several amino acids, where the expression "one to several" includes 1 to 4, 1 to 3, 1 to 2, or 1 in one or more embodiments.

In one or more embodiments, the dimeric green-yellow fluorescent protein according to the present disclosure is one that has an amino acid sequence, which is at least 90%, 91%, 92%, 93%, 94%, 95%, 96%, 97%, 98%, 99%, or 99.5% of identity with the sequence from position 2 to 232 of the amino acid sequence of SEQ ID NO: 1, and has a pH sensitivity (pKa) of 4.0 or less.

In one or more embodiments, the dimeric green-yellow fluorescent protein according to the present disclosure may further include a "mutation that results in a photo-switching type" introduced thereinto. Examples of the above-mentioned "mutation that results in a photo-switching type" include T197A or G, i.e., "T197A or T197G". The position of this mutation is based on the amino acid sequence of SEQ ID NO: 1. In the present disclosure, in the case where simply the phrase "dimeric green-yellow fluorescent protein according to the present disclosure" is used, it may include a dimeric green-yellow fluorescent protein of a photo-switching mutant type.

The present disclosure also relates to imaging methods using a fusion protein, a molecular sensor, a nucleic acid, an expression cassette, a vector, and a transformant relating to the dimeric green-yellow fluorescent protein according to the present disclosure, or molecular sensors using them. These can be the same as in the case of the monomeric green-yellow fluorescent protein according to the present disclosure.

The present disclosure further relates to the following one or more non-limiting embodiments.

[1] A fluorescent protein, having an amino acid sequence from position 2 to 225 of the amino acid sequence of SEQ ID NO: 1, at least a mutation being introduced into the sequence wherein the above-mentioned mutation is selected from the group consisting of F149T or S or A, L158T or S or A, H160T or S or A, Y174T or S or A, and Y192T or S or A as well as combinations of 2 to 5 thereof.

[2] The fluorescent protein according to [1], including the amino acid sequence from position 2 to 225 of the amino acid sequence of SEQ ID NO: 1, a further mutation being introduced into the sequence, wherein the further mutation is selected from the group consisting of K112E or D or Q, E147K or R or Q, Q145E or D, K166E or D or Q, P162L or V or I or A, P223L or V or I or A, N37S or A or G, E140K or R or Q, K185R or A or G, A150/E151/G152→PHGP or PHA, and K180T or S as well as combinations of 2 to 11 thereof.

[3] The fluorescent protein according to [1] or [2], including an amino acid sequence from position 8 to 232 of the amino acid sequence of SEQ ID NO: 2.

[4] The fluorescent protein according to any one of [1] to [3], having a pH sensitivity (pKa) of 4.0 or less, being monomeric, and having a green-yellow fluorescent color.

[5] A fluorescent protein, including an amino acid sequence the amino acid sequence of a fluorescent protein according to any one of [1] to [4], one to several amino acids of the sequence being deleted, substituted and/or added, having a pH sensitivity (pKa) of 4.0 or less, being monomeric, and having a green-yellow fluorescent color.

[6] A fluorescent protein, including an amino acid sequence, which is at least 90%, 91%, 92%, 93%, 94%, 95%, 96%, 97%, 98%, 99%, or 99.5% of identity with the amino acid sequence of a fluorescent protein according to any one of [1] to [4], having a pH sensitivity (pKa) of 4.0 or less, being monomeric, and having a green-yellow fluorescent color.

[7] A fusion protein, including a fluorescent protein according to any one of [1] to [6] fused therein, wherein the portion that is said fluorescent protein is a fluorescent protein that has a pH sensitivity (pKa) of 4.0 or less, is monomeric, and has a green-yellow fluorescent color.

[8] The fluorescent protein according to any one of [1] to [6], having an amino acid sequence from position 2 to 225 of the amino acid sequence of SEQ ID NO: 1, a mutation of T197A or G being introduced into the sequence.

[9] The fluorescent protein according to [8], being capable of functioning as a fluorescent protein that changes from non-fluorescent to fluorescent when irradiated with a light having a specific wavelength, which does not cause fluorescence excitation, and changes from fluorescent to non-fluorescent when irradiated with a light used for fluorescence excitation.

[10] A fusion protein, including a fluorescent protein according to [8] or [9] fused therein, wherein the portion that is said fluorescent protein is a fluorescent protein that has a pH sensitivity (pKa) of 4.0 or less, is monomeric, has a green-yellow fluorescent color, and is capable of functioning as a fluorescent protein that changes from non-fluorescent to fluorescent when irradiated with a light having a specific wavelength, which does not cause fluorescence excitation, and changes from fluorescent to non-fluorescent when irradiated with a light used for fluorescence excitation.

[11] A molecular sensor, including a part or all of the amino acid sequence of a protein according to any one of [1] to [10] and utilizing fluorescence properties of said protein.

[12] A nucleic acid having a base sequence that encodes a protein according to any one of [1] to [10] or a molecular sensor according to [11].

[13] An expression cassette, including a base sequence that encodes a protein according to any one of [1] to [10] or a molecular sensor according to [11].

[14] A vector, being capable of expressing a protein according to any one of [1] to [10] or a molecular sensor according to [11], or including a nucleic acid according to [12] or an expression cassette according to [13].

[15] A transformant, expressing a protein according to any one of [1] to [10] or a molecular sensor according to [11].

[16] A fluorescent protein, including an amino acid sequence from position 2 to 232 of the amino acid sequence of SEQ ID NO: 1.

[17] The fluorescent protein according to [16], having a pH sensitivity (pKa) of 4.0 or less, being dimeric, and having a green-yellow fluorescent color.

[18] A fluorescent protein, including an amino acid sequence from position 2 to 232 of the amino acid sequence of SEQ ID NO: 1, one to several amino acids of the sequence being deleted, substituted, and/or added, having a pH sensitivity (pKa) of 4.0 or less, being dimeric, and having a green-yellow fluorescent color.

[19] A fluorescent protein, including an amino acid sequence of a fluorescent protein according to any one of [16] to [18], one to several amino acids of the sequence being deleted, substituted and/or added, having a pH sensitivity (pKa) of 4.0 or less, being dimeric, and having a green-yellow fluorescent color.

[20] A fluorescent protein, including an amino acid sequence, which is at least 90%, 91%, 92%, 93%, 94%, 95%, 96%, 97%, 98%, 99%, or 99.5% of identity with the amino acid sequence of a fluorescent protein according to any one of [16] to [18], having a pH sensitivity (pKa) of 4.0 or less, being dimeric, and having a green-yellow fluorescent color.

[21] A fusion protein, including a fluorescent protein according to any one of [16] to [20] fused therein, wherein the portion that is said fluorescent protein is a fluorescent protein that has a pH sensitivity (pKa) of 4.0 or less, is dimeric, and has a green-yellow fluorescent color.

[22] The fluorescent protein according to any one of [16] to [20], having an amino acid sequence from position 2 to 225 of the amino acid sequence of SEQ ID NO: 1, a mutation of T197A or G being introduced into the sequence.

[23] The fluorescent protein according to [22], being capable of functioning as a fluorescent protein that changes from non-fluorescent to fluorescent when irradiated with a light having a specific wavelength, which does not cause fluorescence excitation, and changes from fluorescent to non-fluorescent when irradiated with a light used for fluorescence excitation.

[24] A fusion protein, including a fluorescent protein according to [22] or [23] fused therein, wherein the portion that is said fluorescent protein is a fluorescent protein that has a pH sensitivity (pKa) of 4.0 or less, is monomeric, has a green-yellow fluorescent color, and is capable of functioning as a fluorescent protein that changes from non-fluorescent to fluorescent when irradiated with a light having a specific wavelength, which does not cause fluorescence excitation, and changes from fluorescent to non-fluorescent when irradiated with a light used for fluorescence excitation.

[25] A molecular sensor, including a part or all of the amino acid sequence of a protein according to any one of [16] to [24] and using the fluorescent properties of said protein.

[26] A nucleic acid, including a base sequence that encodes a protein according to any one of [16] to [24] or a molecular sensor according to [25].

[27] An expression cassette, including a base sequence that encodes a protein according to any one of [16] to [24] or a molecular sensor according to [25].

[28] A vector, being capable of expressing a protein according to any one of [16] to [24] or a molecular sensor according to [25], or including a nucleic acid according to [26] or an expression cassette according to [27].

[29] A transformant, expressing a protein according to any one of [16] to [24] or a molecular sensor according to [25].

[30] An imaging method, including detecting a fluorescence signal of a protein according to any one of [1] to [10] and [16] to [24] or a molecular sensor according to [11] or [25] from a cell in which the protein, the molecular sensor, a nucleic acid according to [12] or [26], an expression cassette according to [13] or [27], or a vector according to [14] or [28] has been introduced.

[31] A super-resolution imaging or super-resolution live imaging method, including performing photo-switching of a photo-switching mutant-type green-yellow fluorescent protein according to any one of [8] to [10] and [22] to [24] to switch its fluorescence on or off in a cell in which the photo-switching mutant-type fluorescent protein has been introduced, and/or detecting a fluorescence signal of the photo-switching mutant-type fluorescent protein.

Hereinafter, the present disclosure will be described in more detail with reference to examples, but these examples are illustrative and the present disclosure is not limited to these examples.

EXAMPLES

[Cloning of dfGFP]

dfGFP is a fluorescent protein derived from flower hat jelly (scientific name: *Olindias formosa*). First, total RNA was extracted from flower hat jelly, and mRNA was reverse transcribed to DNA using an oligo T primer to prepare a cDNA library. This cDNA library was amplified by PCR and then inserted into a bacterial expression vector. These plasmids were transformed into *Escherichia coli*, and colonies that emit fluorescence were selected to identify the gene that encodes the fluorescent protein dfGFP of the flower hat jelly. The amino acid sequence of dfGFP encoded by said gene is SEQ ID NO: 1 in the Sequence Listing.

[Production of mfGFP]

Mutations F149T, L158T, H160T, Y174T, Y192A, K112E, E147K, Q145E, K166E, P162L, P223L, N37S, E140K, K185R, A150/E151/G152→PHGP, and K180T each were site-specifically introduced into the amino acid sequence of SEQ ID NO: 1 in the Sequence Listing. Furthermore, M at the N-terminus of SEQ ID NO: 1 was substituted with 7 amino acid residues (MVSKGEE SEQ ID NO: 4) at the N-terminus of EGFP, and 7 amino acid residues (EPSASAV SEQ ID NO: 5) at the C-terminus of SEQ ID NO: 1 were substituted with 7 amino acid residues (GMDELYK SEQ ID NO: 6) at C-terminus of EGFP. Thus, a gene that encodes the amino acid sequence of SEQ ID NO: 2 in the Sequence Listing was produced (SEQ ID NO: 3). The amino acid sequence of mfGFP that is encoded by said gene is SEQ ID NO: 2 in the Sequence Listing.

[Purification of mfGFP]

mfGFP having a polyhistidine tag at the N-terminus was introduced into a bacterial expression vector pRSETB to be expressed in *Escherichia coli*. After culturing it in LB medium at 23° C. for 65 hours, bacterial cells were disrupted with a French press, and the supernatant was purified by gel filtration using a Ni-NTA agarose affinity column (manufactured by Qiagen) and a PD-10 column (manufactured by GE Healthcare), and further it was repurified using an AKTA Superdex 200 10/300 GL (GE Healthcare) column.

[Confirmation that mfGFP is Monomeric]

Figure 1:
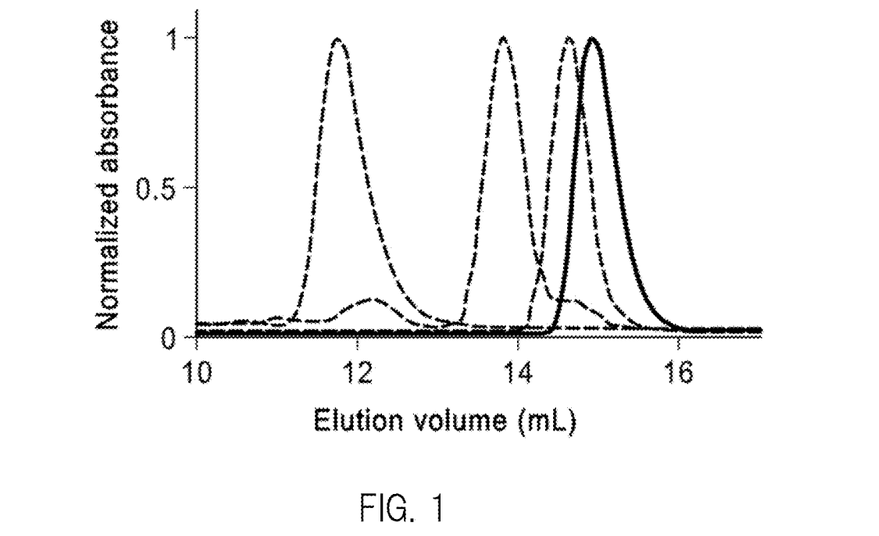
FIG. 1 shows the results of size exclusion gel filtration chromatography of purified fluorescent proteins. The spectra indicated with dotted lines show the absorptions of 10 μM DsRed (tetramer), tdTomato (dimer), and mCherry (monomer) in order from the left. The spectrum indicated with a solid line shows the absorption of mfGFP.

FIG. 1 shows the results of size exclusion gel filtration chromatography using a Superdex 200 10/30 column. The solvent is 20 mM HEPES solution of pH 7.4 containing 150 mM NaCl. The larger the molecular weight/molecular volume, the faster the flow in the column. Therefore, peaks appear on the left side in the figure. The spectra indicated with dotted lines in FIG. 1 show the absorptions of 10 μM DsRed (tetramer), tdTomato (dimer), and mCherry (monomer) in order from the left. The spectrum indicated with a solid line shows the absorption of 10 μM mfGFP. Since the peak position of mfGFP is almost the same as that of mCherry, it can be said that

[mfGFP Physical Property 1]

Figure 2:
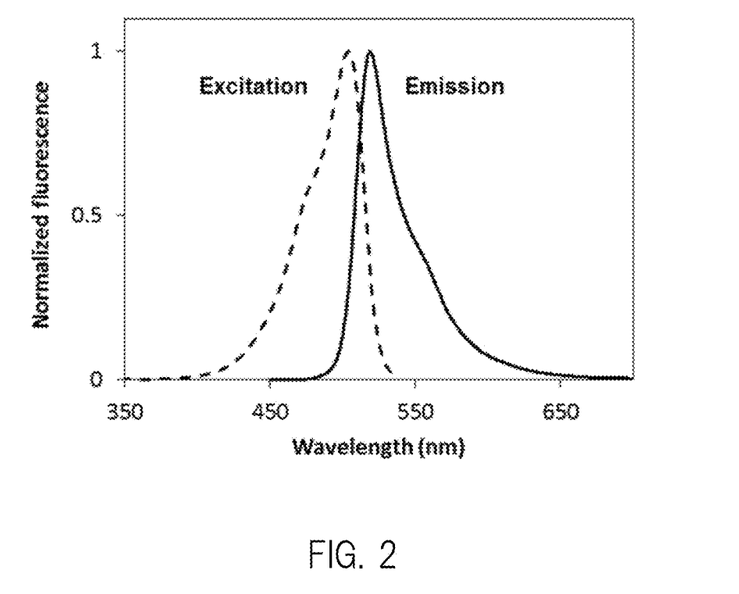
FIG. 2 shows the results of measuring the fluorescence properties of purified mfGFP.

The properties of the purified fluorescent protein were measured. The results are shown in FIG. 2. Measurement using a fluorescence spectrometer showed that mfGFP has an excitation peak of 504 nm and a fluorescence peak of 519 nm. Absorption spectrum measurement showed that the molar extinction coefficient at the absorption peak of mfGFP was 83,000 $M^{-1} \cdot cm^{-1}$ and measurement of the absolute fluorescence quantum yield showed that mfGFP had a quantum yield of 0.90.

[mfGFP Physical Property 2: pH Sensitivity (pKa)]

Figure 3:
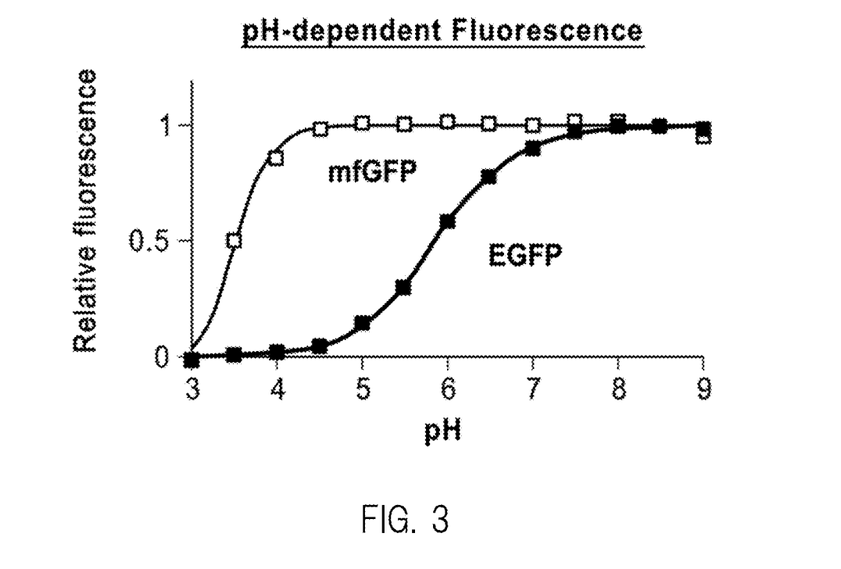
FIG. 3 shows the results of measuring the fluorescence intensity of mfGFP or EGFP, after mfGFP or EGFP was dissolved in buffers of pH 3 to 9.

Using a mixed solution of 30 mM sodium citrate and 30 mM boric acid, pH buffers of pH 3 to 9 were prepared in increments of 0.5. mfGFP or EGFP was dissolved in the above-mentioned each buffer and the fluorescence intensity thereof was measured using a fluorescence spectrometer (FIG. 3). Fitting the data thus obtained to the Hill equation gave a value of pKa=3.5 as the pKa (pH at which the fluorescence intensity of a fluorescent protein becomes half of the maximum value when the pH of a medium in which said fluorescent protein is present changes from basic pH to acidic pH) of mfGFP.

Figure 4:
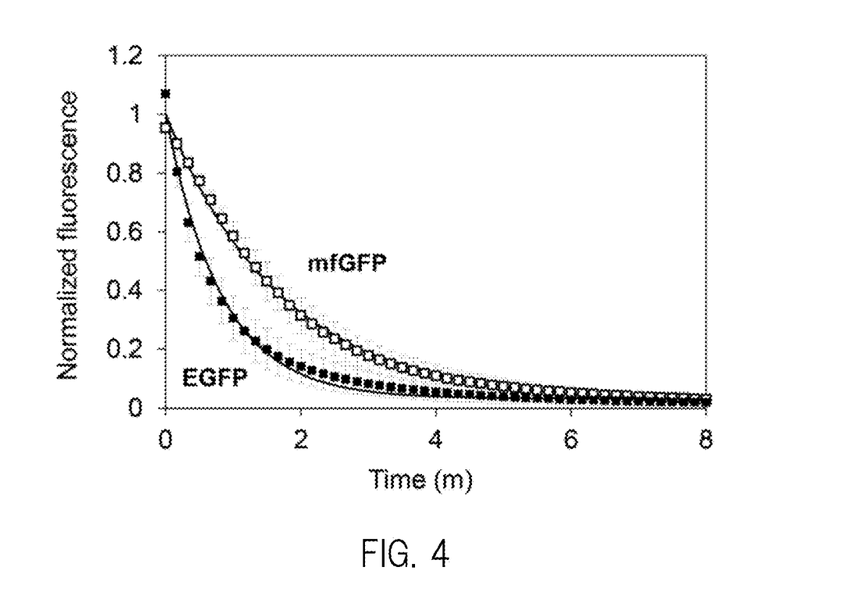
FIG. 4 shows the results of measuring the photostability of mfGFP or EGFP.

[mfGFP Physical Property 3]

mfGFP or EGFP was expressed in the cytoplasm of HeLa cells, which then were irradiated with light using a mercury lamp light and a 440-480 nm bandpass filter, and thereby photostability was examined (FIG. 4). The fluorescence intensity half times of mfGFP and EGFP were 1.2 minutes and 0.6 minute, respectively. This result suggests that the photostability of mfGFP is about two times higher than that of EGFP.

[mfGFP Physical Property 4]

Figure 5:
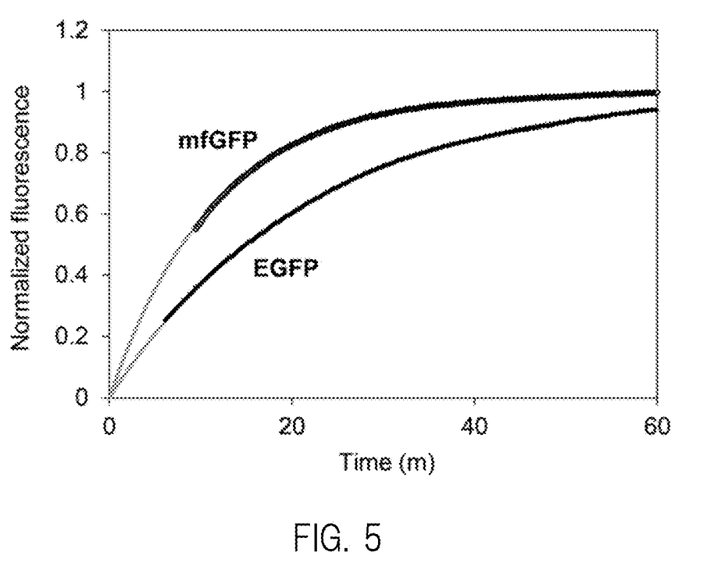
FIG. 5 shows the results of measuring the maturation rate ratio of the fluorophores of mfGFP or EGFP.

The maturation rate ratio of the fluorophore of each of mfGFP and EGFP was examined. Each fluorescent protein was transformed into *Escherichia coli* and cultured in an oxygen-free environment at 37° C. for one day to 1.5 days to prepare a protein in which the fluorophore was immature. Temporal changes of the fluorescence intensity that occur with exposure of the protein to air were measured (FIG. 5). The half-saturation times for mfGFP and EGFP fluorophore maturation was 8.0 minutes and 14.9 minutes, respectively, which therefore suggests excellent fluorophore forming ability of mfGFP.

The optical properties of mfGFP and EGFP are summarized in Table 1 below.

TABLE 1

| Protein | $^a\lambda_{ex}$(nm) | $^b\lambda_{em}$(nm) | $^c\varepsilon$ (mM$^{-1}$ cm$^{-1}$) | $^d\Phi$ | $^e$Brightness | $^f$pK$_a$ | $^g$Photo-stability (m) | $^h$Maturation speed (m) |
|---|---|---|---|---|---|---|---|---|
| EGFP | 488 | 507 | 56 | 0.75 | 42 | 5.9 | 0.6 | 14.9 |
| mfGFP | 504 | 519 | 83 | 0.90 | 75 | 3.5 | 1.2 | 8.0 |

($^a$Excitation peak.
$^b$Emission peak.
$^c$Extinction coefficient determined by alkali-denaturation method.
$^d$Absolute fluorescence quantum yield determined by integrating sphere.
$^e$Product of $\varepsilon$ and $\Phi$.
$^f$pH at which fluorescence intensity become its half-maximal value.
$^g$Photobleaching half-time in live cells under 465/30 nm wide-field mercury-lamp illumination.
$^h$Half-time required for its chromophore formation in oxygen-dependent manner.)

[mfGFP Physical Property 5]

Figure 6:
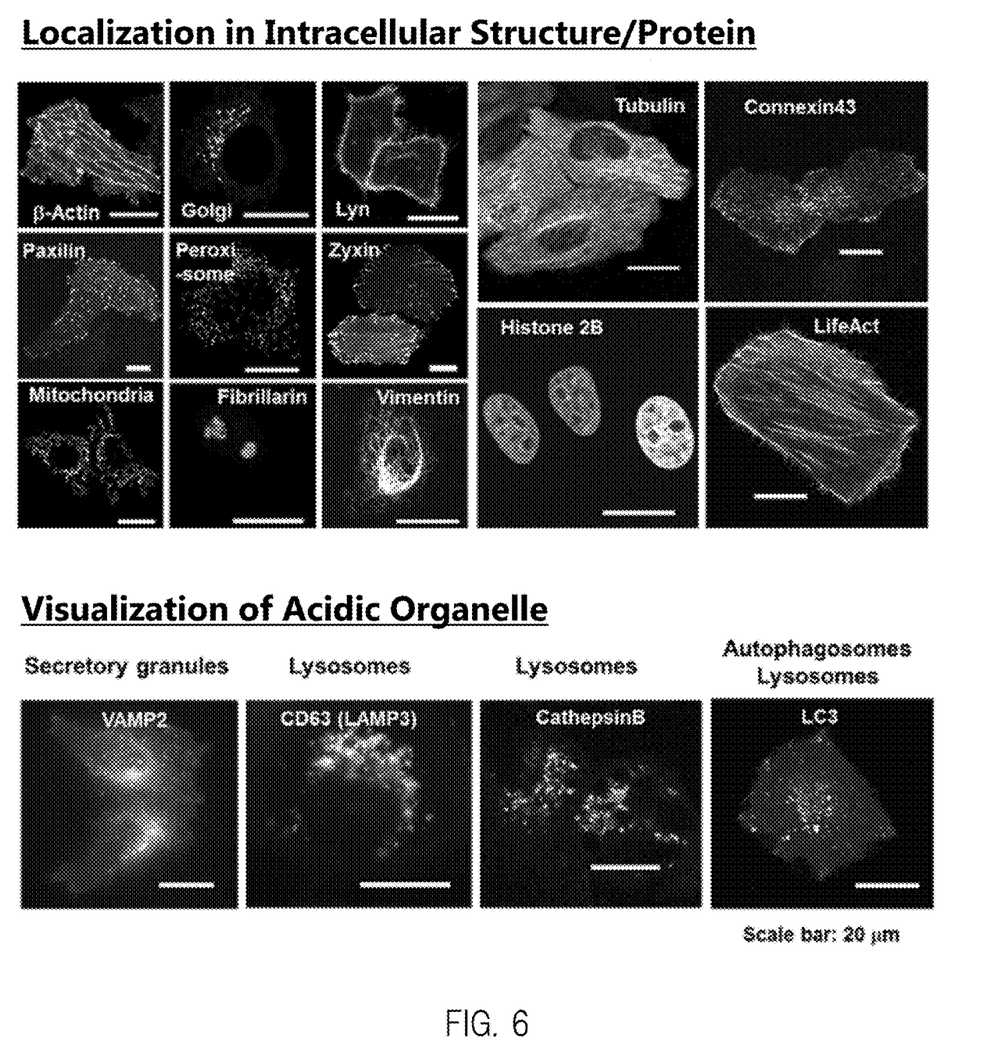
FIG. 6 include images showing the results obtained when localization signals for various organelle proteins were fused to mfGFP to allow HeLa cells to express them.

Localization signals for various organelle proteins were fused to mfGFP and were expressed in HeLa cells (actin, Golgi body, phosphorus, paxillin, peroxisome, zyxin, mitochondria, fibrillarin, vimentin, tubulin, connexin43, histone H2B, LifeAct, VAMP2, LAMP3, CathepsinB, LC3). The results are shown in FIG. 6. As shown in FIG. 6, the mfGFP fusion proteins showed correct localization in the target organelle proteins. Particularly, successful labeling of tubulin, in which localization is difficult, suggests the high properties of mfGFP as a monomer. Furthermore, it also showed high fluorescence intensity even in the secretory vesicles/lysosomes (pH 4.5 to 5.5), inside of which was kept acidic.

[mfGFP Physical Property 6]

Figure 7:
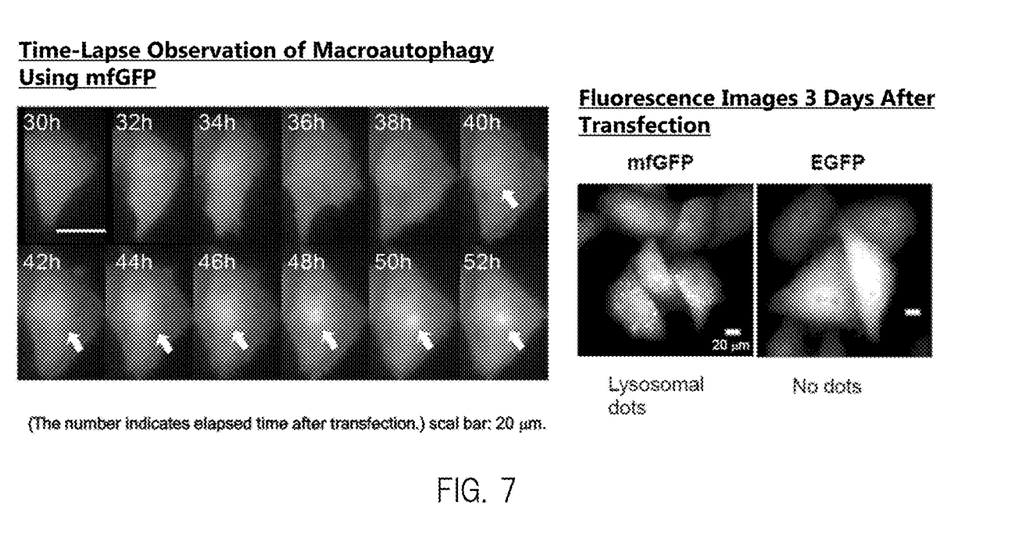
FIG. 7 shows images obtained after allowing mfGFP or EGFP to be expressed in the cytoplasm of HeLa cells and culturing them at 37° C./5% for three days.

After mfGFP or EGFP was expressed in the cytoplasm of HeLa cells and cultured at 37° C./5% for three days, images of lysosome-like fluorescent dots were obtained only for mfGFP (FIG. 7). This is thought to be the result that the fluorescent protein that was present in the cytoplasm was transported to the lysosome by nonselective macroautophagy. Similarly, time-lapse imaging of the process of mfGFP accumulation from cytoplasm to lysosome also was successful (FIG. 7). The pH of the lysosome of HeLa cells was as low as about 4.7, and such dots were not observed in the case of EGFP with high pH sensitivity.

[mfGFP Photo-Switching Mutant]

Introduction of a T197A (or T197G) amino acid mutation into mfGFP resulted in a mutant (photo-switching mutant) capable of controlling the fluorescent/non-fluorescent state thereof in a light wavelength-dependent manner while maintaining the acid tolerance of mfGFP.

Figure 8:
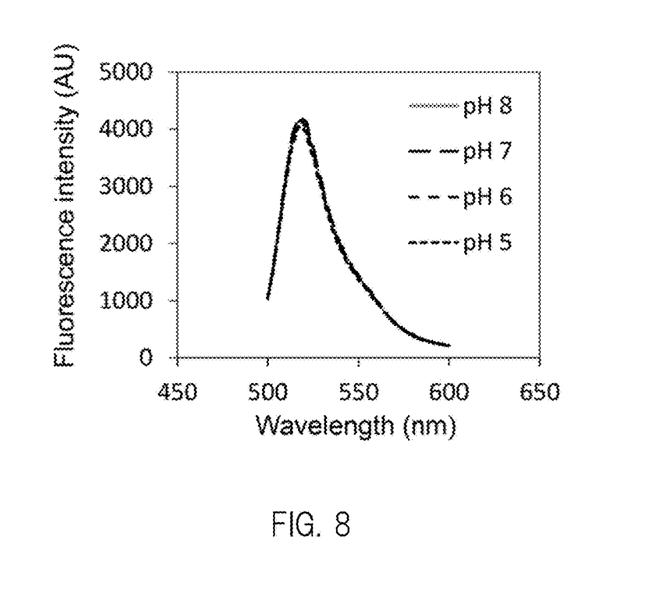
FIG. 8 shows the results of measuring the fluorescence intensity of an mfGFP photo-switching mutant in buffers of pH 5, 6, 7, and 8.
Figure 9:
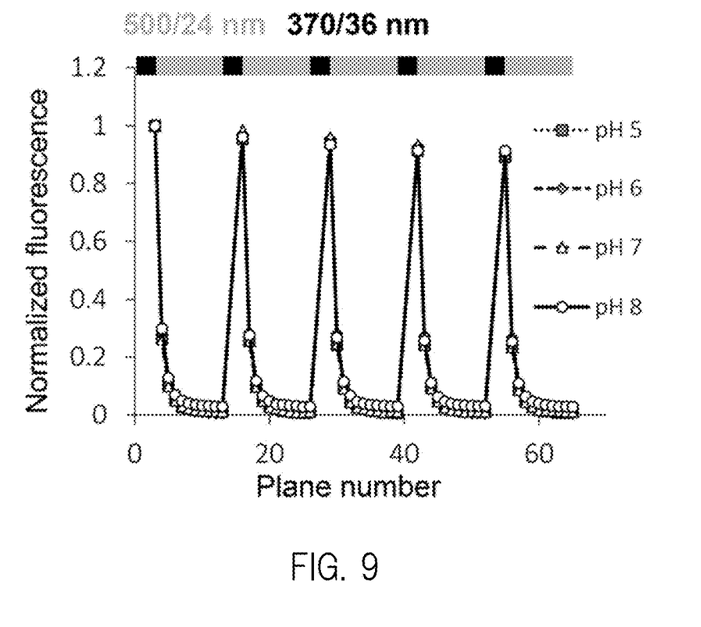
FIG. 9 shows an example of continuous photo-switching of an mfGFP photo-switching mutant in buffers of pH 5, 6, 7, and 8.

When the T197A mutant was expressed in *Escherichia coli* and the extract thereof was mixed with buffers of pH 5, 6, 7, and 8, it was found that the fluorescence intensity was not affected by the pH within the above range (FIG. 8). Furthermore, when the same sample was observed under a microscope, it was found that it shifted to a nonfluorescent state when irradiated with a light of 500/24 nm and shifted to a fluorescent state when irradiated with a light of 370/36 nm (FIG. 9).

[Sequence Listing Free Text]

SEQ ID NO: 1: Amino Acid Sequence of dfGFP
SEQ ID NO: 2: Amino Acid Sequence of mfGFP
SEQ ID NO: 3: Base Sequence of mfGFP

The invention claimed is:

1. A fluorescent protein, comprising the amino acid sequence from position 2 to 225 of the amino acid sequence of SEQ ID NO: 1 and at least a mutation introduced into the sequence based on SEQ ID NO: 1,
   wherein the mutation is selected from the group consisting of F149T or S or A, L158T or S or A, H160T or S or A, Y174T or S or A, and Y192T or S or A, and combinations of 2 to 5 thereof.

2. The fluorescent protein according to claim 1, comprising a further mutation introduced into the sequence based on SEQ ID NO: 1,
   wherein the further mutation is selected from the group consisting of K112E or D or Q, E147K or R or Q, Q145E or D, K166E or D or Q, P162L or V or I or A, P223L or V or I or A, N37S or A or G, E140K or R or Q, K185R or A or G, A150/E151/G152→PHGP or PHA, and K180T or S, and combinations of 2 to 11 thereof.

3. The fluorescent protein according to claim 1, further comprising another mutation introduced into the sequence based on SEQ ID NO: 1, wherein the another mutation is T197A or G.

4. The fluorescent protein according to claim 1, comprising the amino acid sequence from position 8 to 232 of the amino acid sequence of SEQ ID NO: 2.

5. The fluorescent protein according to claim 1, having a pH sensitivity (pKa) of 4.0 or less, being monomeric, and having a green-yellow fluorescent color.

6. The fluorescent protein according to claim 1, wherein one to several amino acids of the sequence is deleted, substituted and/or added, and having a pH sensitivity (pKa) of 4.0 or less, being monomeric, and having a green-yellow fluorescent color.

7. A fusion protein, comprising the fluorescent protein according to claim 1 fused therein, wherein the portion that is said fluorescent protein is a fluorescent protein that has a pH sensitivity (pKa) of 4.0 or less, is monomeric, and has a green-yellow fluorescent color.

8. A fluorescent protein which is:
   a fluorescent protein comprising the amino acid sequence from position 2 to 232 of the amino acid sequence of SEQ ID NO: 1 and at least a T197A or G mutation introduced into the sequence based on SEQ ID NO: 1, or
   a fluorescent protein comprising the amino acid sequence from position 2 to 232 of the amino acid sequence of SEQ ID NO: 1, wherein one to several amino acids of the sequence is deleted, substituted and/or added, and at least a T197A or G mutation is introduced into the sequence based on SEQ ID NO: 1,
   wherein the fluorescent protein has a pH sensitivity (pKa) of 4.0 or less, is dimeric, and has a green-yellow fluorescent color.

9. A molecular sensor, comprising a part or all of the amino acid sequence of the fluorescent protein according to claim 1 and having the fluorescent properties of said fluorescent protein.

10. A nucleic acid, comprising a base sequence that encodes the fluorescent protein according to claim 1.

11. An expression cassette, comprising the nucleic acid sequence according to claim 10.

12. A vector, comprising the nucleic acid sequence according to claim 10.

13. An isolated cell, comprising the nucleic acid sequence according to claim 10, wherein the isolated cell expresses the fluorescent protein.

* * * * *

SEQUENCE LISTING

```
<160> NUMBER OF SEQ ID NOS: 3

<210> SEQ ID NO 1
<211> LENGTH: 232
<212> TYPE: PRT
<213> ORGANISM: Olindias formosa

<400> SEQUENCE: 1

Met Ala Ser Gly Arg Ala Leu Phe Gln Tyr Pro Met Thr Ser Lys Ile
1               5                   10                  15

Glu Leu Asn Gly Glu Ile Asn Gly Lys Lys Phe Lys Val Ala Gly Glu
                20                  25                  30

Gly Phe Thr Pro Asn Ser Gly Arg Phe Asn Met His Ala Tyr Cys Thr
            35                  40                  45

Thr Gly Asp Leu Pro Met Ser Trp Val Val Ile Ala Ser Pro Leu Gln
        50                  55                  60

Tyr Gly Phe His Met Phe Ala His Tyr Pro Glu Asp Ile Thr His Phe
65                  70                  75                  80

Phe Gln Glu Cys Phe Pro Gly Ser Tyr Thr Leu Asp Arg Thr Leu Arg
                85                  90                  95

Met Glu Gly Asp Gly Thr Leu Thr Thr His His Glu Tyr Ser Leu Lys
            100                 105                 110
```

```
Asp Gly Cys Val Thr Ser Lys Thr Thr Leu Asn Ala Ser Gly Phe Asp
            115                 120                 125

Pro Lys Gly Ala Thr Met Thr Lys Ser Phe Val Glu Gln Leu Pro Asn
130                 135                 140

Gln Val Glu Ile Phe Ala Glu Gly Asn Gly Ile Arg Leu Leu Ser His
145                 150                 155                 160

Val Pro Tyr Leu Lys Lys Asp Gly Thr Ile Gln Ile Gly Tyr Gln Asp
                165                 170                 175

Cys Ile Val Lys Pro Val Gly Gly Lys Lys Val Thr Gln Pro Lys Tyr
            180                 185                 190

His Phe Leu His Thr Gln Ile Ile Gln Lys Lys Asp Pro Asn Asp Thr
        195                 200                 205

Arg Asp His Ile Val Gln Thr Glu Leu Ala Val Ala Gly Asn Pro Trp
210                 215                 220

His Glu Pro Ser Ala Ser Ala Val
225                 230

<210> SEQ ID NO 2
<211> LENGTH: 239
<212> TYPE: PRT
<213> ORGANISM: Artificial Sequence
<220> FEATURE:
<223> OTHER INFORMATION: derived from dfGFP

<400> SEQUENCE: 2

Met Val Ser Lys Gly Glu Glu Ala Ser Gly Arg Ala Leu Phe Gln Tyr
1               5                   10                  15

Pro Met Thr Ser Lys Ile Glu Leu Asn Gly Glu Ile Asn Gly Lys Lys
                20                  25                  30

Phe Lys Val Ala Gly Glu Gly Phe Thr Pro Ser Ser Gly Arg Phe Asn
            35                  40                  45

Met His Ala Tyr Cys Thr Thr Gly Asp Leu Pro Met Ser Trp Val Val
    50                  55                  60

Ile Ala Ser Pro Leu Gln Tyr Gly Phe His Met Phe Ala His Tyr Pro
65                  70                  75                  80

Glu Asp Ile Thr His Phe Phe Gln Glu Cys Phe Pro Gly Ser Tyr Thr
                85                  90                  95

Leu Asp Arg Thr Leu Arg Met Gly Asp Gly Thr Leu Thr Thr His
            100                 105                 110

His Glu Tyr Ser Leu Glu Asp Gly Cys Val Thr Ser Lys Thr Thr Leu
        115                 120                 125

Asn Ala Ser Gly Phe Asp Pro Lys Gly Ala Thr Met Thr Lys Ser Phe
    130                 135                 140

Val Lys Gln Leu Pro Asn Glu Val Lys Ile Thr Pro His Gly Pro Asn
145                 150                 155                 160

Gly Ile Arg Leu Thr Ser Thr Val Leu Tyr Leu Lys Glu Asp Gly Thr
                165                 170                 175

Ile Gln Ile Gly Thr Gln Asp Cys Ile Val Thr Pro Val Gly Gly Arg
            180                 185                 190

Lys Val Thr Gln Pro Lys Ala His Phe Leu His Thr Gln Ile Ile Gln
        195                 200                 205

Lys Lys Asp Pro Asn Asp Thr Arg Asp His Ile Val Gln Thr Glu Leu
    210                 215                 220

Ala Val Ala Gly Asn Leu Trp His Gly Met Asp Glu Leu Tyr Lys
225                 230                 235
```

<210> SEQ ID NO 3
<211> LENGTH: 720
<212> TYPE: DNA
<213> ORGANISM: Artificial Sequence
<220> FEATURE:
<223> OTHER INFORMATION: derived from dfGFP

<400> SEQUENCE: 3

```
atggtgagca agggcgagga ggcatctggc agagccctgt tccagtaccc catgaccagc      60
aagatcgagc tgaacggcga gatcaacggc aagaaattca aggtggccgg cgagggcttc     120
accccagca gcggcagatt caacatgcac gcctactgca ccaccggcga cctgcctatg      180
agctgggtcg tgattgccag ccccctccag tacggcttcc acatgttcgc ccactacccc     240
gaggacatca cacttttt ccaggaatgc ttccccggca gctacaccct ggaccggacc       300
ctgagaatgg aaggcgacgg cacctgacc acccaccacg agtacagcct ggaggacggc      360
tgcgtgacct ccaagaccac cctgaatgcc agcggcttcg accctaaggg cgccaccatg     420
accaagagct tcgtgaaaca actgcctaac gaggtgaaga tcacccccca cggccccaac     480
ggcatcagac tgaccagcac cgtgctgtac ctgaaggagg atggcaccat ccagatcggc     540
acccaggact gcatcgtgac ccctgtgggc ggaaggaaag tgacccagcc caaggcccac     600
ttcctgcaca cccagatcat ccagaagaag gacccaacg acacccggga ccacatcgtg      660
cagacagaac tggccgtggc cggcaatctg tggcacggca tggacgagct gtacaagtaa     720
```